US009119558B2

(12) United States Patent
Yoshida et al.

(10) Patent No.: US 9,119,558 B2
(45) Date of Patent: Sep. 1, 2015

(54) ULTRASONIC DIAGNOSTIC APPARATUS AND ULTRASONIC DIAGNOSTIC METHOD

(75) Inventors: Tetsuya Yoshida, Nasushiobara (JP); Naohisa Kamiyama, Otawara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 401 days.

(21) Appl. No.: 12/705,074

(22) Filed: Feb. 12, 2010

(65) Prior Publication Data

US 2010/0204579 A1   Aug. 12, 2010

(30) Foreign Application Priority Data

Feb. 10, 2009  (JP) .................................. 2009-028034

(51) Int. Cl.
| | |
|---|---|
| *A61B 8/00* | (2006.01) |
| *A61B 8/08* | (2006.01) |
| *A61B 17/34* | (2006.01) |
| *G01S 7/52* | (2006.01) |

(52) U.S. Cl.
CPC .............. *A61B 8/0833* (2013.01); *A61B 8/0841* (2013.01); *A61B 17/3403* (2013.01); *G01S 7/52074* (2013.01); *G01S 7/52085* (2013.01); *A61B 2017/3413* (2013.01); *G01S 7/52038* (2013.01)

(58) Field of Classification Search
USPC .......................................... 600/407, 437–475
See application file for complete search history.

(56) References Cited

U.S. PATENT DOCUMENTS

| | | | | |
|---|---|---|---|---|
| 5,761,331 A | * | 6/1998 | Clark, III ....................... | 382/131 |
| 2006/0241451 A1 | | 10/2006 | Nakaya et al. | |
| 2008/0319317 A1 | * | 12/2008 | Kamiyama et al. ........... | 600/443 |

FOREIGN PATENT DOCUMENTS

| | | |
|---|---|---|
| EP | 1 416 443 A1 | 5/2004 |
| JP | 6-205776 | 7/1994 |

(Continued)

OTHER PUBLICATIONS

Office Action issued Jun. 4, 2013, in Japanese patent Application No. 2009-028034.

(Continued)

*Primary Examiner* — Mark Remaly
(74) *Attorney, Agent, or Firm* — Oblon, McClelland, Maier & Neustadt, L.L.P.

(57) ABSTRACT

An ultrasonic diagnostic apparatus has an ultrasonic probe, a control unit, a basic image generating unit, a differential image generating unit, and a composite image generating unit. The control unit controls the ultrasonic probe so as to sequentially perform, every scanning line of scanning lines in a scanning region, a transmitting and receiving under a first transmitting/receiving condition, a second transmitting/receiving condition, and a third transmitting/receiving condition. The basic image generating unit generates a first image based on the first transmitting/receiving condition, a second image based on the second transmitting/receiving condition, and a third image based on the third transmitting/receiving condition. The differential image generating unit performs a differential processing based on the first image and the second image to generate a differential image. The composite image generating unit performs a composite processing based on the differential image and the third image to generate a composite image.

20 Claims, 12 Drawing Sheets

(56) References Cited

FOREIGN PATENT DOCUMENTS

| JP | 2001-61841 A | 3/2001 |
| JP | 2006-288679 A | 10/2006 |
| JP | 2006-320378 A | 11/2006 |
| JP | 2007-301122 A | 11/2007 |
| JP | 2008-12150 | 1/2008 |

OTHER PUBLICATIONS

Office Action issued Aug. 27, 2013 in Japanese Patent Application No. 2009-028034.

* cited by examiner

ULTRASONIC DIAGNOSTIC APPARATUS AND ULTRASONIC DIAGNOSTIC METHOD

BACKGROUND OF THE INVENTION

1. Field of the Invention

The present invention relates to a technique capable of a two-dimensional (2D) scanning and a real time three-dimensional (3D) scanning, and more particularly to an ultrasonic diagnostic apparatus and an ultrasonic diagnostic method that emphatically displays a needle-tip portion of a puncture needle so that an operator can easily visually recognize a position of the needle-tip portion.

2. Description of the Related Art

An ultrasonic diagnostic apparatus is a medical diagnostic apparatus that noninvasively obtains tomograms of a soft tissue in a living body from a body surface using an ultrasonic pulse-echo method. The ultrasonic diagnostic apparatus has features that the apparatus is compact and inexpensive, has high safety with no exposure to X-rays, is capable of blood flow imaging, or the like as compared with other medical diagnostic apparatuses, and has been widely used in cardiac, abdominal, urology, obstetrics and gynecology departments, or the like.

The ultrasonic diagnostic apparatus is used not only for image diagnosis but also, for example, for radiofrequency ablation (RFA) as a local therapy of hepatocellular cancer or a biopsy for hepatocellular tissue examination. Such a therapy and an examination require precise puncture into a region of interest such as a tumor using a puncture needle. Thus, to clearly ascertain where the puncture needle enters in the living body, an ultrasonic diagnostic apparatus that can monitor the region of interest and the puncture needle in real time is used. Particularly, in recent years, the ultrasonic diagnostic apparatus sometimes uses real time three-dimensional ultrasonic images for display because of faster computers. In such a case, some methods have been proposed of displaying a puncture needle position on three-dimensional data during a puncture therapy, or marking a direction of a puncture needle (for example, Japanese Patent Application Publication (Laid-open: KOKAI) No. 6-205776). The ultrasonic diagnostic apparatus that is easy to use and capable of easy observation in real time is often used for a biopsy, or monitoring the needle-tip portion of a puncture needle and a lesion position in a local ablation therapy for cancer.

In recent years, an ultrasonic diagnostic apparatus capable of a real time volume scanning has also appeared. This apparatus can obtain needle position information in a slice direction of an ultrasonic probe, which has been hard to obtain, and is expected to increase accuracy of a biopsy or an ablation therapy.

However, the ultrasonic diagnostic apparatus in the related art sometimes has poor visibility because the visualized needle-tip portion of the puncture needle is buried in a background image, or the like, and places a burden on an operator. Also, because of uncertainty about the precise position of the needle-tip portion of the puncture needle, sufficient therapeutic effects may not be obtained such that tissue in a different position from the position of planned tissue is removed or an ablation therapy is performed in a different position.

When the ultrasonic diagnostic apparatus capable of the real time volume scanning is used, there is a problem that an expected effect cannot be obtained due to insufficient visibility of the needle-tip portion of the puncture needle.

Further, various studies have been made to increase visibility of a needle-tip portion of a puncture needle, and for example, there is a method using an image processing filter such as edge reinforcement. However, such a method has not been put to practical use because separation of only the needle-tip portion is difficult, and a substantial portion other than the needle-tip portion is influenced.

SUMMARY OF THE INVENTION

The present invention is achieved in view of such circumstances, and has an object to provide an ultrasonic diagnostic apparatus and an ultrasonic diagnostic method that allows an operator to easily visually recognize the position of a needle-tip portion of a puncture needle in monitoring the puncture needle.

To solve the above-described problems, the present invention provides the ultrasonic diagnostic apparatus comprising: an ultrasonic probe configured to transmit an ultrasonic pulse to a two-dimensional scanning region or a three-dimensional scanning region, and receive an echo corresponding to the ultrasonic pulse as a received signal; a control unit configured to control the ultrasonic probe so as to sequentially perform, every scanning line of scanning lines in the scanning region, the transmitting and receiving under a first transmitting/receiving condition, the transmitting and receiving under a second transmitting/receiving condition which is different from the first transmitting/receiving condition, and the transmitting and receiving under a third transmitting/receiving condition which is different from the first transmitting/receiving condition and the second transmitting/receiving condition; a basic image generating unit configured to generate a first image based on the received signal under the first transmitting/receiving condition, a second image based on the received signal under the second transmitting/receiving condition, and a third image based on the received signal under the third transmitting/receiving condition; a differential image generating unit configured to perform a differential processing based on the first image and the second image to generate a differential image; and a composite image generating unit configured to perform a composite processing based on the differential image and the third image to generate a composite image.

To solve the above-described problems, the present invention provides the ultrasonic diagnostic apparatus comprising: an ultrasonic probe configured to transmit an ultrasonic pulse to a two-dimensional scanning region or a three-dimensional scanning region, and receive an echo corresponding to the ultrasonic pulse as a received signal; a control unit configured to control the ultrasonic probe so as to successively perform, every scanning line of scanning lines in the scanning region, the transmitting and receiving under a first transmitting/receiving condition, and the transmitting and receiving under a third transmitting/receiving condition which is different from the first transmitting/receiving condition; a basic image generating unit configured to generate a first image based on the received signal under the first transmitting/receiving condition, and a third image based on the received signal under the third transmitting/receiving condition; and a composite image generating unit configured to perform a composite processing based on the first image and the third image to generate a composite image.

To solve the above-described problems, the present invention provides the ultrasonic diagnostic method comprising steps of: controlling which controls an ultrasonic probe which transmits an ultrasonic pulse to a two-dimensional scanning region or a three-dimensional scanning region, and receives an echo corresponding to the ultrasonic pulse as a received signal so as to sequentially perform, every scanning line of scanning lines in the scanning region, the transmitting and receiving under a first transmitting/receiving condition, the transmitting and receiving under a second transmitting/receiving condition which is different from the first transmitting/receiving condition, and the transmitting and receiving under a third transmitting/receiving condition which is different from the first transmitting/receiving condition and the second transmitting/receiving condition; basic image generating which generates a first image based on the received signal under the first transmitting/receiving condition, a second image based on the received signal under the second transmitting/receiving condition, and a third image based on the received signal under the third transmitting/receiving condition; differential image generating which performs a differential processing based on the first image and the second image to generate a differential image; and composite image generating which performs a composite processing based on the differential image and the third image to generate a composite image.

To solve the above-described problems, the present invention provides the ultrasonic diagnostic method comprising steps of: controlling which controls an ultrasonic probe which transmits an ultrasonic pulse to a two-dimensional scanning region or a three-dimensional scanning region, and receives an echo corresponding to the ultrasonic pulse as a received signal so as to sequentially perform, every scanning line of scanning lines in the scanning region, the transmitting and receiving under a first transmitting/receiving condition, and the transmitting and receiving under a third transmitting/receiving condition which is different from the first transmitting/receiving condition; basic image generating which generates a first image based on the received signal under the first transmitting/receiving condition, and a third image based on the received signal under the third transmitting/receiving condition; and composite image generating which performs a composite processing based on the first image and the third image to generate a composite image.

DETAILED DESCRIPTION OF THE PREFERRED EMBODIMENTS

An embodiment of an ultrasonic diagnostic apparatus and an ultrasonic diagnostic method according to the present invention will be described with reference to the accompanying drawings.

Figure 1:
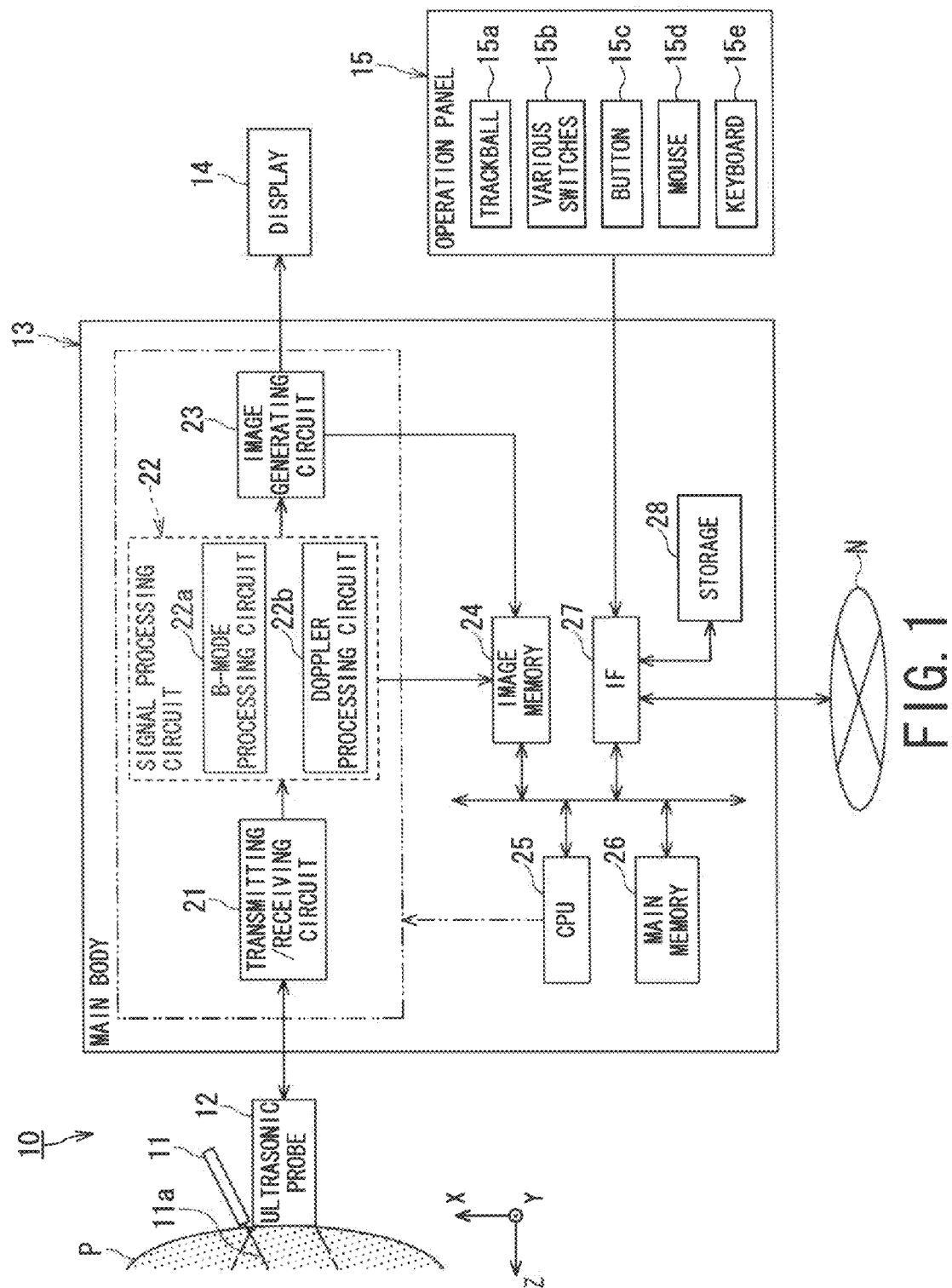
FIG. 1 is a schematic diagram showing a configuration of ultrasonic diagnostic apparatus of the present embodiment.

FIG. 1 is a schematic diagram showing a configuration of ultrasonic diagnostic apparatus of the present embodiment.

FIG. 1 shows an ultrasonic diagnostic apparatus 10 of the present embodiment. The ultrasonic diagnostic apparatus 10 mainly has a puncture adaptor 11, an ultrasonic probe 12, a main body 13, a display 14, and an operation panel 15.

The puncture adaptor 11 is, for example, secured to the ultrasonic probe 12 at a predetermined angle. To the puncture adaptor 11, a puncture needle 11a to be inserted into a region from a body surface of an object (patient) P to a puncture target (tumor) in the body is mounted.

The ultrasonic probe 12 has a plurality of piezoelectric transducers that transmit ultrasonic pulses to a two-dimensional or a three-dimensional scanning region including the puncture target of the patient P based on drive pulses from the main body 13, and receive echoes corresponding to the transmitted ultrasonic pulses, and convert the echoes into electric signals. When the piezoelectric transducers in the ultrasonic probe 12 transmit the ultrasonic pulses to the scanning region, ultrasonic beams formed by the ultrasonic pulses are successively reflected by a discontinuous surface of acoustic impedance of body tissue. The reflected echoes are received by the piezoelectric transducers. The received echo is converted into an echo signal by the piezoelectric transducers. An amplitude of the echo signal depends on a difference in acoustic impedance on the reflecting discontinuous surface. When the ultrasonic beam is reflected by moving blood flow or a surface such as a cardiac wall, an echo corresponding to the transmitted ultrasonic pulse depends on a speed component in an ultrasonic transmitting direction of a mobile object by the Doppler effect, and undergoes frequency deviation.

The ultrasonic probe 12 includes, for example, a mechanical three-dimensional probe and a two-dimensional probe (matrix array probe). The mechanical three-dimensional probe is a probe that can mechanically sweep many (for example, 100 to 200) piezoelectric transducers arranged only in an X-axis direction (azimuth direction), or a probe that can mechanically sweep many piezoelectric transducers arranged in the X-axis direction and a few (for example, 3) piezoelectric transducers arranged in a Y-axis direction (elevation direction). The two-dimensional probe is a probe having many piezoelectric transducers arranged in both the X-axis direction and the Y-axis direction.

When the ultrasonic probe 12 is the mechanical three-dimensional probe, the many piezoelectric transducers arranged in the X-axis direction obtain electronic focus so as to cause the ultrasonic pulse to converge in the X-axis direction to form an appropriate ultrasonic beam extending in a Z-axis direction (depth direction). Meanwhile, when the ultrasonic probe 12 is the mechanical three-dimensional probe, it is preferable that an acoustic lens is provided on an ultrasonic irradiation side of one piezoelectric transducer in the Y-axis direction or the piezoelectric transducer is formed as a concave type so as to cause the ultrasonic pulse to converge in the Y-axis direction to form an appropriate ultrasonic beam extending in the Z-axis direction. When the ultrasonic probe 12 is the mechanical three-dimensional probe, an acoustic lens is provided on an ultrasonic irradiation side of a few piezoelectric transducers in the Y-axis direction, or the number of driven piezoelectric transducers among the few piezoelectric transducers is changed in the Y-axis direction depending on the position of a focus in the Z-axis direction so as to cause the ultrasonic pulse to converge in the Y-axis direction to form an appropriate ultrasonic beam extending in the Z-axis direction. In scanning a three-dimensional region using the mechanical three-dimensional probe, a plurality of two-dimensional cross-sections (X-Z cross-sections) are scanned by the ultrasonic beam formed by the ultrasonic pulse while the piezoelectric transducers is swept.

When the ultrasonic probe 12 is the two-dimensional probe, the many piezoelectric transducers arranged in the X-axis direction and the Y-axis direction obtain electronic focus so as to cause the ultrasonic pulse to converge in the X-axis direction and the Y-axis direction to form an appropriate ultrasonic beam extending in the Z-axis direction. In scanning the three-dimensional region using the two-dimensional probe, a plurality of X-Z cross-sections are scanned by the ultrasonic beam formed by the ultrasonic pulse while a transmission surface of the ultrasonic pulse is electronically shifted in the Y-axis direction.

The main body 13 has a transmitting/receiving circuit 21, a signal processing circuit 22, an image generating circuit 23, an image memory 24, a central processing unit (CPU) 25, a main memory 26, an interface (IF) 27, and a storage 28. In the present embodiment, the transmitting/receiving circuit 21, the signal processing circuit 22, and the image generating circuit 23 are configured as integrated circuits for description, but all or part thereof may function by execution of a modularized software program.

The transmitting/receiving circuit 21 has a transmitting circuit and a receiving circuit, not shown. The transmitting circuit has a pulser circuit, a transmission delay circuit, a trigger generating circuit, or the like, not shown. The pulser circuit repeatedly generates rate pulses for forming transmitting ultrasonic at a predetermined rate frequency fr [Hz] (cycle: 1/fr [sec]). The transmission delay circuit provides each rate pulse with a delay time required for focusing the ultrasonic into the beam for each channel and determining a transmission directivity. The trigger generating circuit applies a drive pulse to the piezoelectric transducer in the ultrasonic probe 12 at timing based on the rate pulse.

The transmitting circuit in the transmitting/receiving circuit 21 has a function of instantaneously changing a transmission frequency, a transmission drive voltage (sound pressure), a transmission pulse rate, a scanning region, and the number of flashes according to instructions from the CPU 25. Particularly, the sound pressure is changed by a transmitting portion of linear amplifier type that can instantaneously change the value of the sound pressure or a mechanism that electrically switches a plurality of power supply portions.

The receiving circuit in the transmitting/receiving circuit 21 has an amplifier, a receiving delay circuit, an analog to digital (A/D) conversion circuit, an addition circuit, or the like, not shown. The amplifier amplifies an echo signal captured via the ultrasonic probe 12 for each channel. The receiving delay circuit provides the echo signal amplified by the amplifier with a delay time required for determining a receiving directivity. The A/D conversion circuit converts the echo signal output from the receiving delay circuit into a digital signal. The addition circuit performs an addition processing of the digital echo signal. The addition by the addition circuit enhances a reflection component from a direction according to the receiving directivity of the echo signal, the receiving directivity and the transmitting directivity form an overall beam for ultrasonic transmitting and receiving, and a radio frequency (RF) signal is generated.

The signal processing circuit 22 has a B-mode processing circuit 22a and a Doppler processing circuit 22b. The B-mode processing circuit 22a performs logarithmetic amplification and envelope detection or the like of the RF signal obtained from the transmitting/receiving circuit 21, and generates a B-mode image with signal intensity expressed by brightness. In this case, a visualized frequency band can be changed by changing a detection frequency. Detection processes with two detection frequencies may be performed for one receiving data in parallel.

The Doppler processing circuit 22b performs frequency analysis of speed information from the RF signal obtained from the transmitting/receiving circuit 21, extracts blood flow, tissue, or a contrast medium echo component by the Doppler effect, and calculates blood flow information such as an average speed, dispersion and power for many points. The Doppler processing circuit 22b generates an average speed image, a dispersion image, and a power image as blood flow information and a Doppler image as a combination thereof.

The image generating circuit 23 converts a cross-sectional image of a scan line signal sequence of ultrasonic scanning, which is output from the signal processing circuit 22, into a cross-sectional image of a scan line signal sequence in a general video format typified in, for example, televisions. The image generating circuit 23 includes a memory (not shown) that stores an image. For example, after a diagnosis, an operator (or a user) can call up an image recorded during an examination. Further, the image generating circuit 23 forms volume data on the basis of the cross-sectional images.

The image memory 24 is a storage device that stores images output from the signal processing circuit 22 and the image generating circuit 23. In the image memory 24, images obtained under different transmitting/receiving conditions are stored in parallel. The image memory 24 stores a cross-sectional image of data format before conversion that is referred to as so-called RAW data output from the signal processing circuit 22, a cross-sectional image of data format after video format conversion output from the image generating circuit 23, and volume data based on the cross-sectional image of data format after the video format conversion output from the image generating circuit 23.

The CPU 25 is a control device having a configuration of an integrated circuit (LSI) in which an electronic circuit configured by a semiconductor is sealed in a package having a plurality of terminals. The CPU 25 has a function of executing a program stored in the main memory 26. Alternatively, the CPU 25 has a function of loading a program stored in the storage 28 and a program transferred from a network N, received by the IF 27 and installed in the storage 28, into the main memory 26, and performing the programs.

The main memory 26 is a storage device having a configuration that also serves as a read only memory (ROM), a random access memory (RAM), or the like. The main memory 26 has a function of storing initial program loading (IPL: large scale integration), basic input/output system (BIOS) and data, or temporarily storing a work memory or data of the CPU 25.

The IF 27 is configured by a connector of parallel connection specifications or serial connection specifications. The IF 27 is an interface relating to the operation panel 15, the network N such as a basic local area network (LAN) of a hospital, the storage 28, or the like. The image generated by the main body 13 can be transferred to other systems via the network N by the IF 27.

The storage 28 is a storage device having a configuration in which a metal disk with a magnetic material applied or evaporated is irremovably installed in a reading device (not shown). The storage 28 has a function of storing a program (including an application program and also an OS (operating system) or the like) installed in the main body 13. The OS may be provided with a graphical user interface (GUI) that can use many graphics in displaying information for the operator, and can perform a basic operation with the operation panel 15.

The main memory 26 or the storage 28 store a control program such as an ultrasonic diagnosis program, diagnosis information (patient identification (ID), doctor's observation, or the like), a diagnosis protocol, a transmitting/receiving condition, and other groups of data. Further, the data stored in the main memory 26 or the storage 28 can be transferred to the network N via the IF 27.

The display 14 may be a liquid crystal display or a cathode ray tube (CRT). The display 14 has a function of displaying two-dimensional data or three-dimensional data together with character information or scales of various parameters based on a video signal from the image generating circuit 23.

The operation panel 15 may be a trackball 15a, various switches 15b, a button 15c, a mouse 15d, a keyboard 15e, or the like. The operation panel 15 is connected to the main body 13, and has a function of inputting various instructions from the operator, for example, a setting instruction of a region of interest (ROI), a setting instruction of an image quality condition to the main body 13. The operator can input a transmission frequency of the ultrasonic pulse transmitted from the ultrasonic probe 12, a transmission drive voltage (sound pressure), a transmission pulse rate, a scanning region, puncture mode start and contrast medium flush instructions, a receiving condition, or the like to the main body 13 via the operation panel 15.

Figure 2:
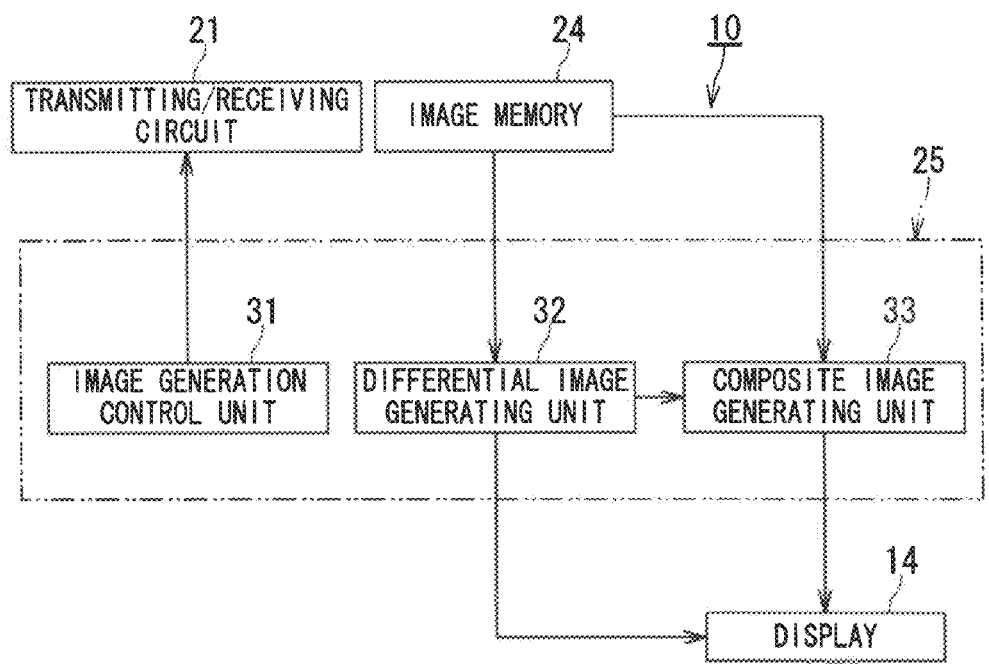
FIG. 2 is a block diagram showing a function of the ultrasonic diagnostic apparatus of the present embodiment.

FIG. 2 is a block diagram showing a function of the ultrasonic diagnostic apparatus 10 of the present embodiment.

The CPU 25 shown in FIG. 1 executes a program, and thus the ultrasonic diagnostic apparatus 10 functions as an image generation control unit 31, a differential image generating unit 32, and a composite image generating unit 33. The differential image generating unit 32 is not a component essential to the ultrasonic diagnostic apparatus 10. In the present embodiment, the units 31 to 33 function by execution of a modularized software program for description, but all or part thereof may be configured by hardware such as an integrated circuit.

The image generation control unit 31 has a function of controlling the transmitting/receiving circuit 21 so as to sequentially perform, for each raster (scanning line), ultrasonic transmitting and receiving under a first transmitting/receiving condition in which a reflection signal from the needle-tip portion of the puncture needle 11a is relatively stronger than a substantial portion other than the needle-tip portion, ultrasonic transmitting and receiving under a second transmitting/receiving condition in which the reflection signal from the needle-tip portion of the puncture needle 11a is relatively weaker than the substantial portion, and ultrasonic transmitting and receiving under a third transmitting/receiving condition different from the first transmitting/receiving condition and the second transmitting/receiving condition. The image generation control unit 31, for example, causes the transmitting/receiving circuit 21 to perform the ultrasonic transmitting and receiving under the first transmitting/receiving condition at a low frequency, and the ultrasonic transmitting and receiving under the second transmitting/receiving condition at a high frequency.

The image generation control unit 31 changes at least one of a transmitting condition and a receiving condition included in the transmitting/receiving condition to set the first transmitting/receiving condition, the second transmitting/receiving condition, and the third transmitting/receiving condition. The transmitting condition includes, for example, a frequency (fundamental frequency), a transmission pulse waveform, a transmission pulse phase, a transmission frequency, the number of transmission burst waves, the number of transmission drive elements (transmission opening), a transmission focus (transmission delay), or the like. The receiving condition includes, for example, a receiving frequency, the number of receiving burst waves, the number of receiving drive elements (receiving opening), a receiving focus (receiving delay), or the like.

Figure 3:
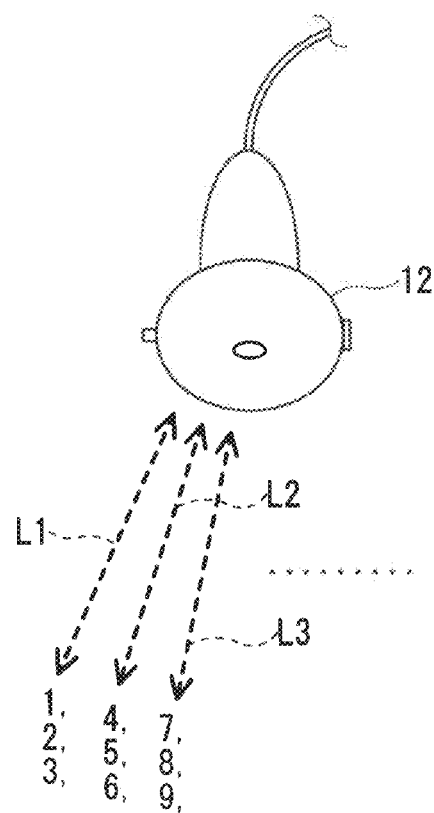
FIG. 3 is a diagram showing an example of a scan sequence.

FIG. 3 is a diagram showing an example of a scan sequence.

As shown in FIG. 3, the ultrasonic probe 12 is controlled by the image generation control unit 31 to perform, for a first raster L1, the ultrasonic transmitting and receiving under the first transmitting/receiving condition, then performs the ultrasonic transmitting and receiving under the second transmitting/receiving condition, and then performs the ultrasonic transmitting and receiving under the third transmitting/receiving condition. Then, the ultrasonic probe 12 is controlled by the image generation control unit 31 to perform, for a second raster L2, the ultrasonic transmitting and receiving under the first transmitting/receiving condition, then performs the ultrasonic transmitting and receiving under the second transmitting/receiving condition, and then performs the ultrasonic transmitting and receiving under the third transmitting/receiving condition. Then, the ultrasonic probe 12 is controlled by the image generation control unit 31 to perform, for a third raster L3, the ultrasonic transmitting and receiving under the first transmitting/receiving condition, then performs the ultrasonic transmitting and receiving under the second transmitting/receiving condition, and then performs the ultrasonic transmitting and receiving under the third transmitting/receiving condition. The order of the ultrasonic transmitting and receiving for each raster is not limited to that shown in FIG. 3, but for example, an order may be conceivable of the ultrasonic transmitting and receiving under the second transmitting/receiving condition, the ultrasonic transmitting and receiving under the third transmitting/receiving condition, and the ultrasonic transmitting and receiving under the first transmitting/receiving condition.

Also, the image generation control unit 31 shown in FIG. 2 has a function of controlling the signal processing circuit 22 and the image generating circuit 23 to generate a first image (first cross-sectional image, first volume data) based on a received (echo) signal by scanning under the first transmitting/receiving condition, a second image (second cross-sectional image, second volume data) based on a received signal by scanning under the second transmitting/receiving condition, and a third image (third cross-sectional image, third volume data) based on a received signal by scanning under the third transmitting/receiving condition and store the images in the image memory 24.

The image generation control unit 31 may set transmitting conditions of the first transmitting/receiving condition, the second transmitting/receiving condition, and the third transmitting/receiving condition to be identical, and set receiving conditions thereof to be different. In this case, three types of images corresponding to the three transmitting/receiving conditions can be obtained by one ultrasonic transmission. Thus, it takes only one third of transmission time in the case with different transmitting conditions of the first transmitting/receiving condition, the second transmitting/receiving condition, and the third transmitting/receiving condition, and there is an advantage that a differential processing or a composite processing can be performed at a general frame rate (volume rate for volume data).

Also, with the identical transmitting conditions of the first transmitting/receiving condition, the second transmitting/receiving condition, and the third transmitting/receiving condition and the different receiving conditions thereof, the image generation control unit 31 sets the first transmitting/receiving condition as a condition for visualizing a low frequency band of the echo signal, and sets the second transmitting/receiving condition and the third transmitting/receiving condition as conditions for visualizing a relatively narrow and high frequency band of the echo signal. Alternatively, with the identical transmitting conditions of the first transmitting/receiving condition, the second transmitting/receiving condition, and the third transmitting/receiving condition and the different receiving conditions thereof, the image generation control unit 31 sets a relatively broad beam sound field and a relatively broad receiving opening of the ultrasonic probe 12 as the first transmitting/receiving condition, and sets a relatively narrow beam sound field and a relatively narrow receiving opening of the ultrasonic probe 12 as the second transmitting/receiving condition and the third transmitting/receiving condition.

Figure 4:
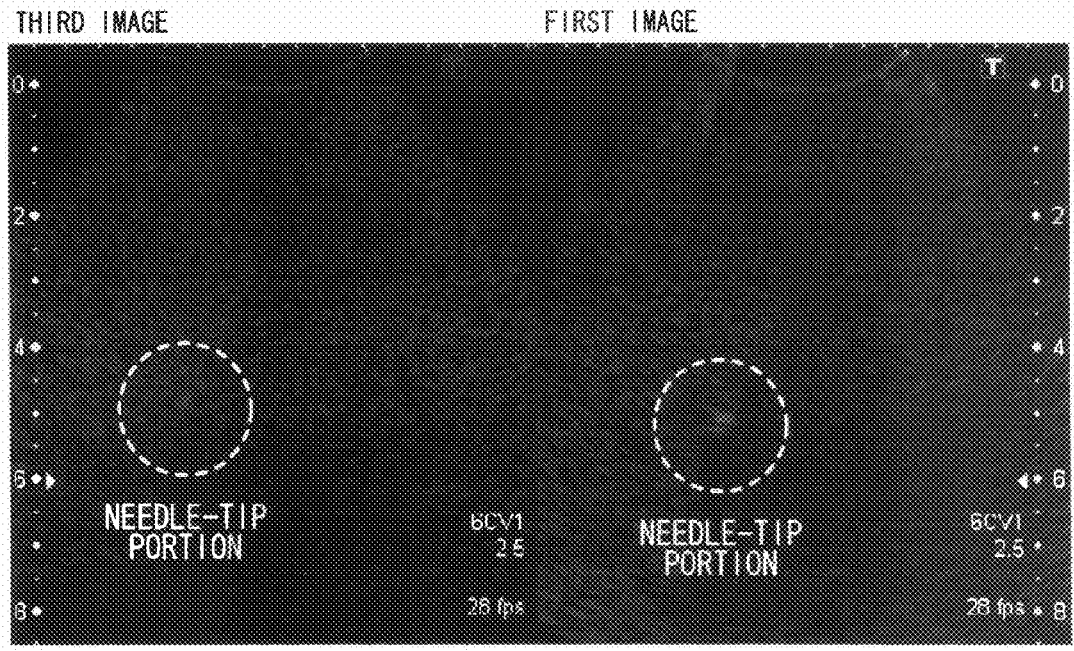
FIG. 4 is diagrams showing examples of images generated by an image generating circuit controlled by an image generation control unit.

FIG. 4 is diagrams showing examples of images generated by the image generating circuit 23 controlled by the image generation control unit 31. The left side in FIG. 4 shows a third image generated with the puncture needle 11*a* inserted into an agar phantom as the object P, and the right side in FIG. 4 shows a first image generated with the puncture needle 11*a* inserted into the agar phantom.

In the first image on the right side in FIG. 4, there is not a large difference in density in the phantom part other than the needle-tip portion of the puncture needle 11*a*, but there is a large difference in density in only the needle-tip portion. In the first image on the right side in FIG. 4, the needle-tip portion of the puncture needle 11*a* can be clearly differentiated from the phantom part as compared with the third image shown on the left side in FIG. 4.

Figure 5:
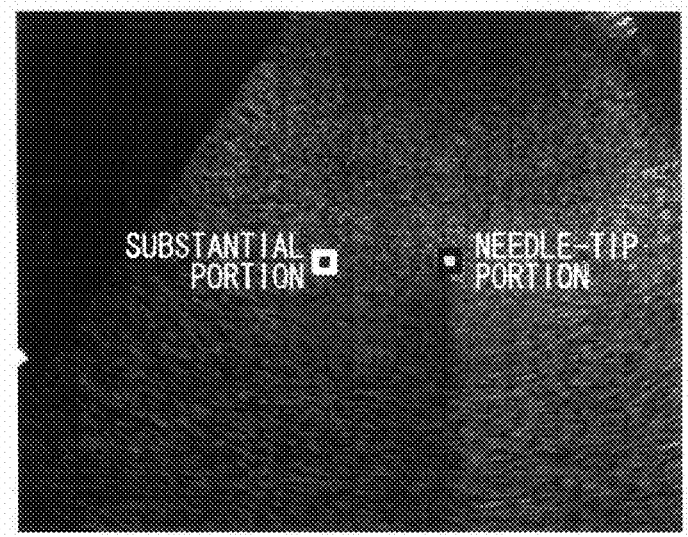
FIG. 5 is a diagram showing an example of an image of liver plotted at two points (needle-tip portion of puncture needle and substantial portion)
Figure 6:
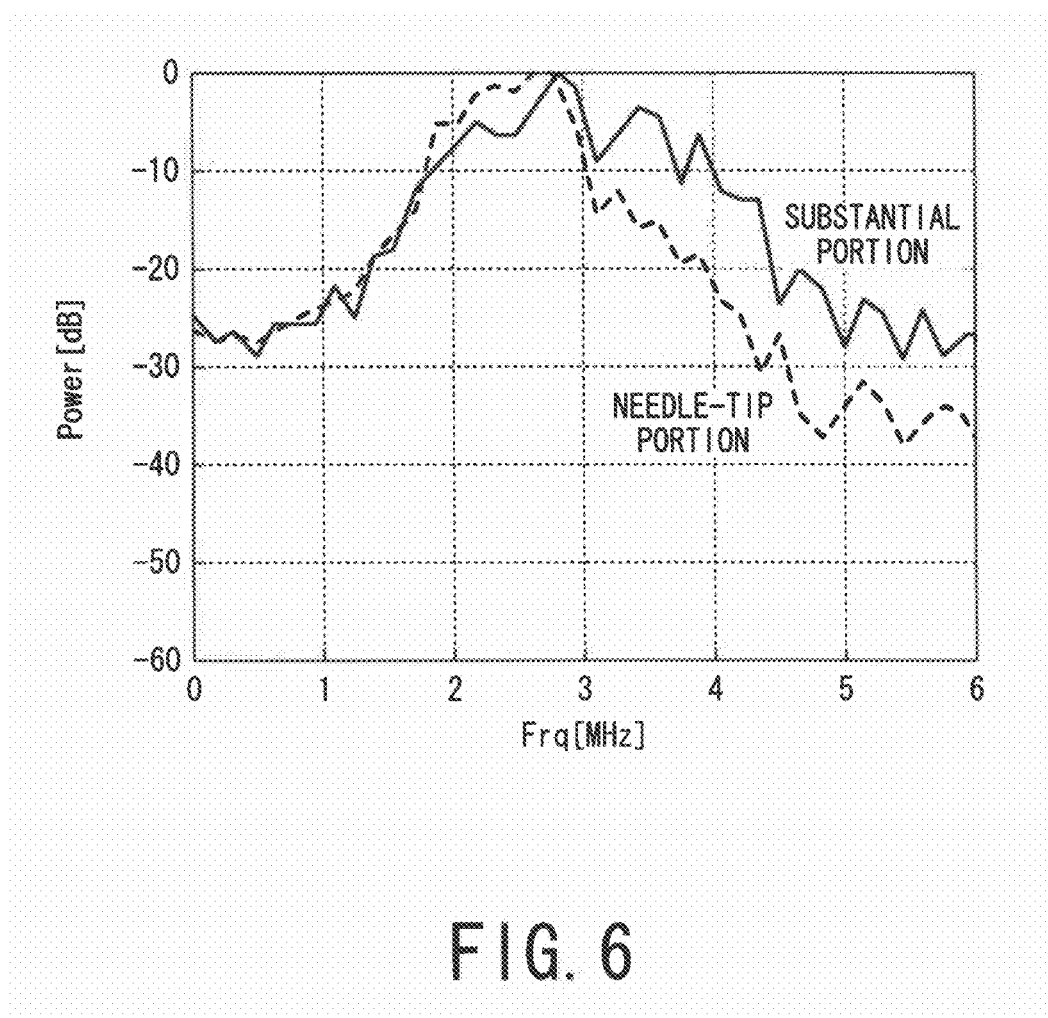
FIG. 6 is a diagram showing an example of frequency spectrums of RF signals from the needle-tip portion and the substantial portion.

FIG. 5 is a diagram showing an example of an image of the liver plotted at two points (needle-tip portion of the puncture needle 11*a* and substantial portion). FIG. 6 is a diagram showing an example of frequency spectrums of RF signals from the needle-tip portion and the substantial portion.

As show in FIG. 6, the RF signal from the needle-tip portion includes fewer high frequency components than the RF signal from the substantial portion other than the needle-tip portion of the puncture needle 11*a*. This is because fewer harmonic components are generated from the needle-tip portion of the puncture needle 11*a*, or an ultrasonic beam spreads more at a low frequency to allow reflection signals scattering at the needle-tip portion of the puncture needle 11*a* to be easily received. Thus, when a visualized frequency band is set to a narrow and relatively high frequency band, an image with fewer signals from the needle-tip portion of the puncture needle 11*a* can be obtained, which is suitable for the second or third transmitting/receiving condition. Meanwhile, when a relatively low frequency band is visualized, an image with the needle-tip portion of the puncture needle 11*a* clearly differentiated can be obtained, which is suitable for the first transmitting/receiving condition.

Figure 7:
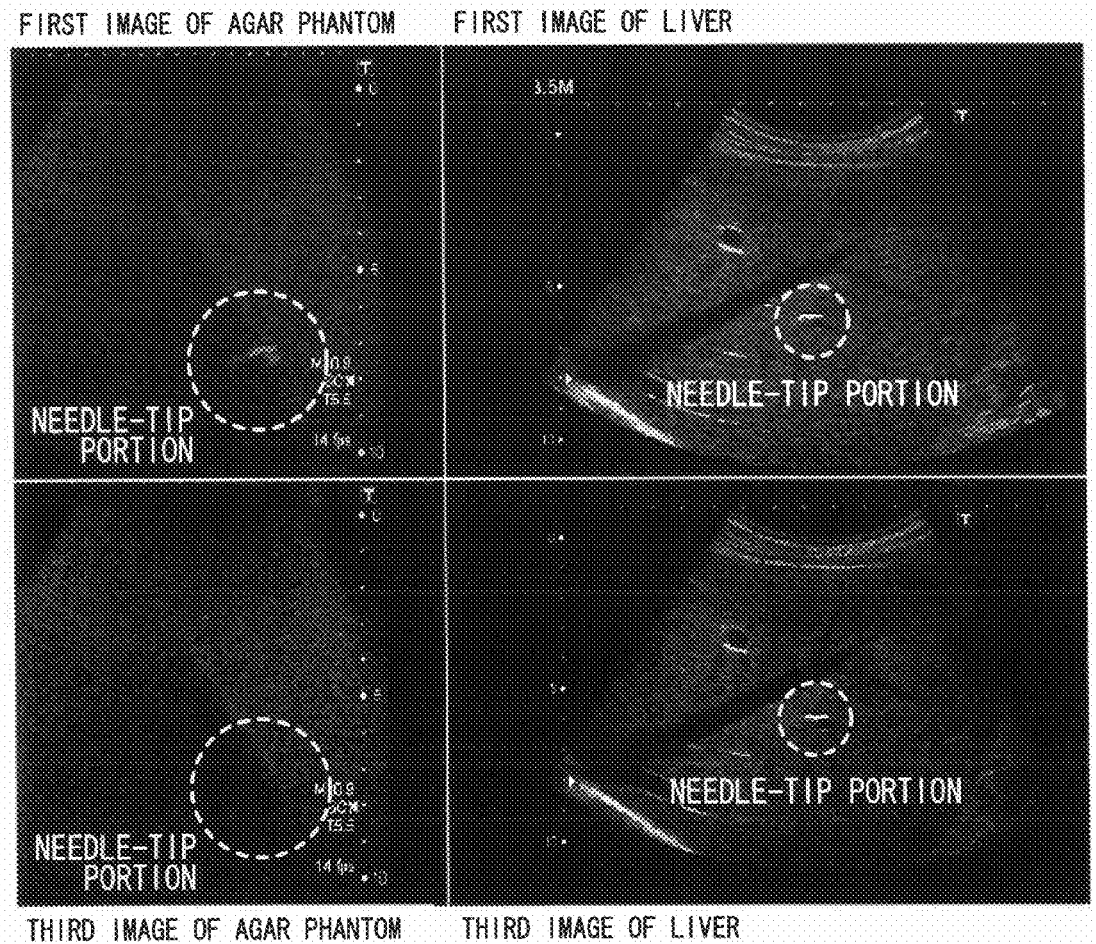
FIG. 7 is diagrams showing examples of images generated by the image generating circuit controlled by the image generation control unit.

FIG. 7 is diagrams showing examples of images generated by the image generating circuit 23 controlled by the image generation control unit 31.

The upper left side in FIG. 7 shows a first image of an agar phantom into which the puncture needle 11*a* is inserted, generated under the first transmitting/receiving condition, and the lower left side in FIG. 7 shows a third image of the agar phantom into which the puncture needle 11*a* is inserted, generated under the third transmitting/receiving condition. The upper right side in FIG. 7 shows a first image of the liver as a object P, generated under the first transmitting/receiving condition, and the lower right side in FIG. 7 shows a third image of the liver, generated under the third transmitting/receiving condition.

Comparing the first image and the third image of the agar phantom shown on the upper and lower left sides in FIG. 7, the needle-tip portion of the puncture needle 11*a* is clearly differentiated in the first image, while the needle-tip portion of the puncture needle 11*a* is not clear in the third image as described above. Comparing the first image and the third image of the liver shown on the upper and lower right sides in FIG. 7, few differences are found therebetween although there is a slight difference such as speckle sizes due to a difference in resolution.

The differential image generating unit 32 shown in FIG. 2 has a function of performing a differential processing of the first image and the second image stored in the image memory 24 controlled by the image generation control unit 31 to generate a differential image (differential cross-sectional image, differential volume data). Alternatively, the differential image generating unit 32 has a function of performing gain correction of the first image and the second image generated by the image generating circuit 23 controlled by the image generation control unit 31 so that the substantial portions have approximately the same brightness, and then performing the differential processing of a first corrected image (first corrected volume data) based on the first image and a second corrected image (second corrected volume data) based on the second image to generate a differential image. Note that the differential image generating unit 32 may perform the differential processing based on the first image and the second image converted into a general video format, or based on the first image the second image as RAW data.

Figure 8:
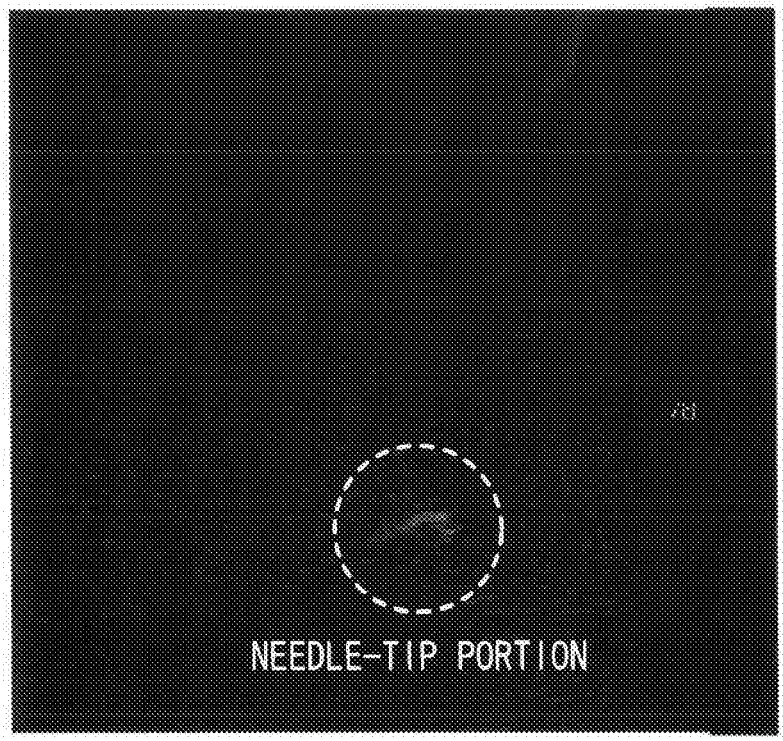
FIG. 8 is diagrams showing examples of differential images.
Figure 8:
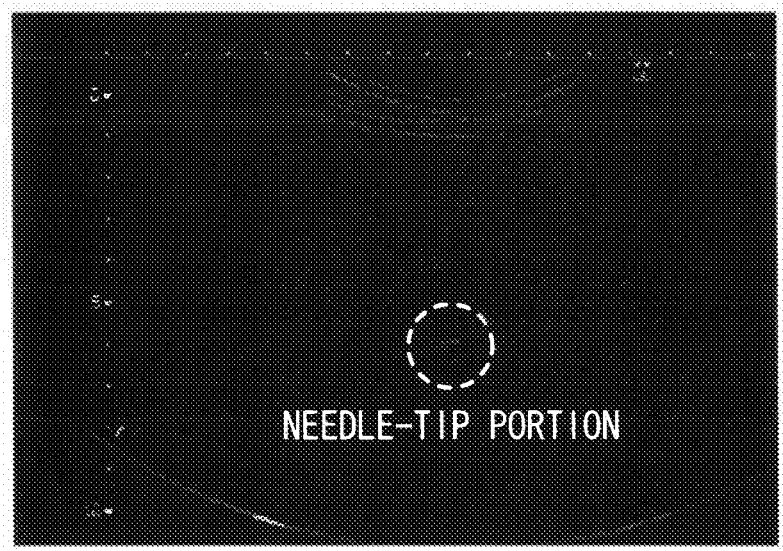

FIG. 8 is diagrams showing examples of the differential images.

From the differential image of the agar phantom shown on the left side in FIG. 8 and the differential image of the liver shown on the right side in FIG. 8, the needle-tip portion of the puncture needle 11*a* is extracted in the differential image of the agar phantom although a little noise is included, while tissue is canceled in the differential image of the liver. Specifically, when the puncture needle 11*a* is inserted in the living body, only the puncture needle 11*a* can be extracted in the differential image.

The composite image generating unit 33 shown in FIG. 2 has a function of executing a composite processing based on the differential image generated by the differential image generating unit 32, and the third image stored in the image memory 24 controlled by the image generation control unit 31 to generate a composite image. Alternatively, the composite image generating unit 33 has a function of executing a composite processing based on the first image and the third image stored in the image memory 24 controlled by the image generation control unit 31 to generate a composite image. When the three-dimensional scanning is performed under the control by the image generation control unit 31, the composite image generating unit 33 performs the composite processing based on predetermined cross-section included in differential volume data as the differential image generated by the differential image generating unit 32, and predetermined cross-section included in third volume data as the third image stored in the image memory 24 controlled by the image generation control unit 31 to generate the composite image.

Figure 9:
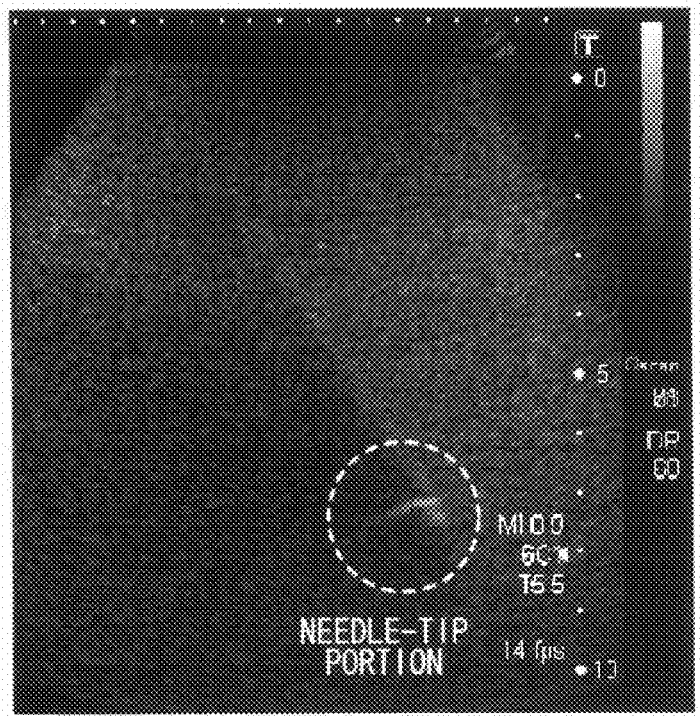
FIG. 9 is a diagram showing an example of a composite image.

FIG. 9 is a diagram showing an example of the composite image.

As shown in FIG. 9, when the differential image formed by the needle-tip portion of the puncture needle 11a is visualized with a different color tone from that of the third image, the operator can easily visually recognize the position of the needle-tip portion of the puncture needle 11a. In the related art, monitoring a path of the puncture needle 11a requires use of a transmitting/receiving condition with lower image quality than that for general observation of the living body by lowering a frequency or spreading the beam so that the needle-tip portion of the puncture needle 11a is easily recognized, which is not suitable for displaying a substantial portion. However, when the composite image generating unit 33 generates the composite image to be displayed, the differential image effective for displaying the needle-tip portion of the puncture needle 11a and the third image obtained under the third transmitting/receiving condition effective for displaying the substantial portion can be displayed in a superimposed manner. Note that the operator may operate the switch 15b or the like of the operation panel 15 to switch display of the differential image, the composite image, the first image (first corrected image), the second image (second corrected image), and the third image at arbitrary timing.

Figure 10:
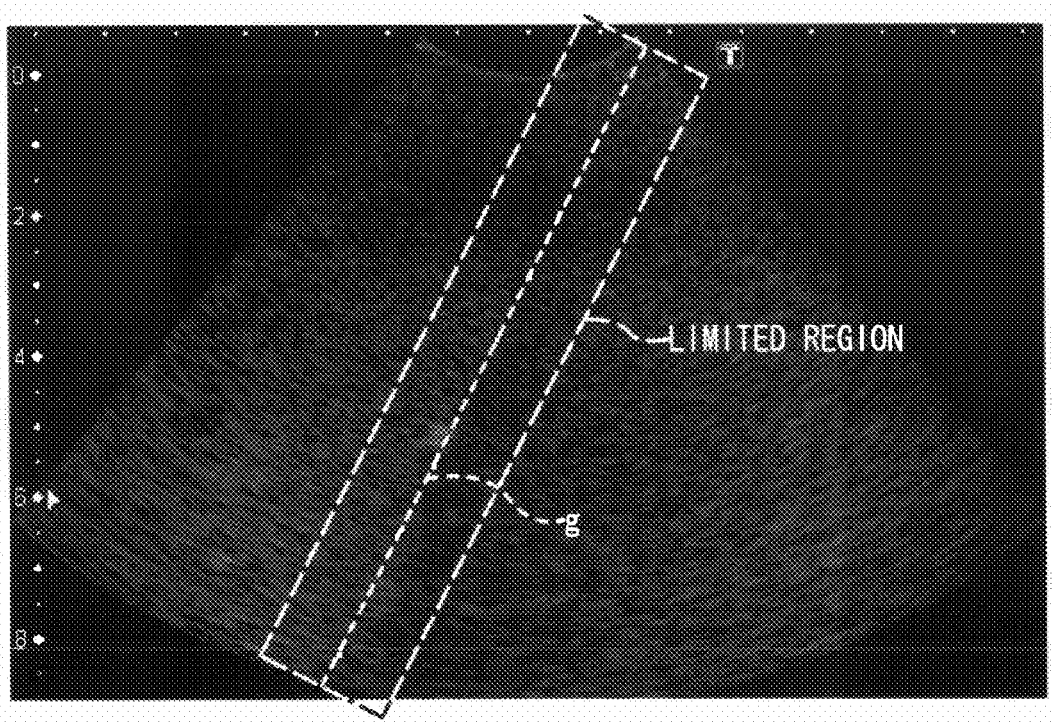
FIG. 10 is a diagram showing a limited region including a puncture guideline of a puncture needle in the differential image.

When the puncture needle 11a is actually inserted into the living body as the object P, the substantial portion is not completely cancelled and remains on the differential image in the differential processing by the differential image generating unit 32 in some cases. Thus, the composite image generating unit 33 may set a limited region including a puncture guideline g (shown in FIG. 10) of the puncture needle 11a in the differential image to perform the composite processing based on the differential image of the limited region and the third image. The composite image generating unit 33 may perform a filtering processing for removing a relatively high frequency band (frequency band higher than a threshold) from the differential image. In this case, the composite image generating unit 33 performs the composite processing based on the differential image after the filtering processing and the third image. The composite image generating unit 33 may perform the filtering processing of only the limited region including the puncture guideline G rather than the entire differential image, and perform the composite processing based on the differential image of the limited region after the filtering processing and the third image of the entire region.

With the ultrasonic diagnostic apparatus 10 of the present embodiment, the needle-tip portion of the puncture needle 11a can be easily separated from the substantial portion on the differential image, and thus an actual (present) inserted needle-tip portion of the puncture needle 11a can be detected by positional information of the puncture adaptor 11 including the puncture needle 11a using the differential image. Thus, when the differential volume data is generated under the control by the image generation control unit 31, the composite image generating unit 33 can recognize the coordinate of the needle-tip portion of the puncture needle 11a based on the differential volume data. For example, the composite image generating unit 33 calculates the center of gravity of the needle-tip portion of the puncture needle 11a detected by performing preprocessing such as a noise removal processing or a binarization processing of the differential volume data as a first coordinate [x1, y1, z1] (first coordinate [x1, y1] for the differential cross-sectional image) of the needle-tip portion of the puncture needle 11a. Since the positional relationship between the puncture adaptor 11 and the ultrasonic probe 12 is already known, the composite image generating unit 33 can calculate a second coordinate [x2, y2, z2] on the puncture adaptor 11 through which the needle-tip portion of the puncture needle 11a always passes.

Figure 11:
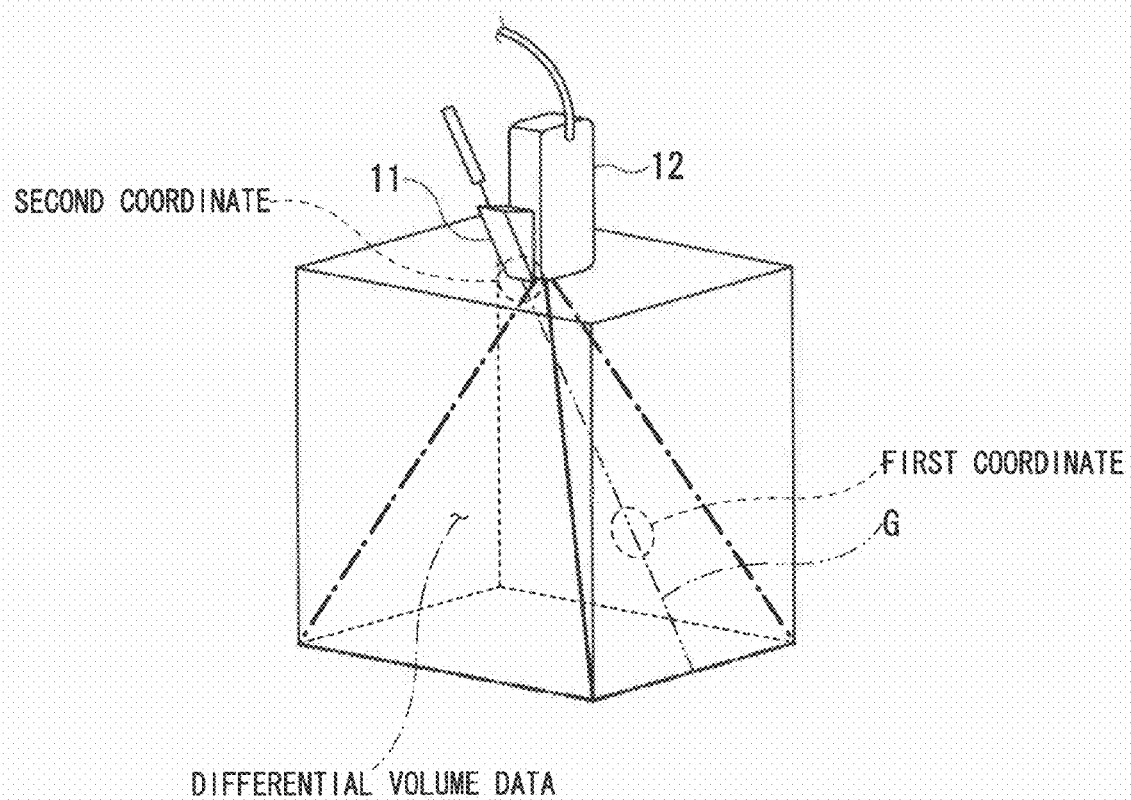
FIG. 11 is a diagram showing an actual puncture line of the present embodiment based on a first coordinate and a second coordinate in differential volume data.

As described above, the composite image generating unit 33 can recognize an actual puncture line G (shown in FIG. 11) in the present embodiment passing through the first coordinate and the second coordinate based on the calculated first coordinate and second coordinate in the differential volume data. The puncture line G is displayed on the display 14.

Figure 12A:
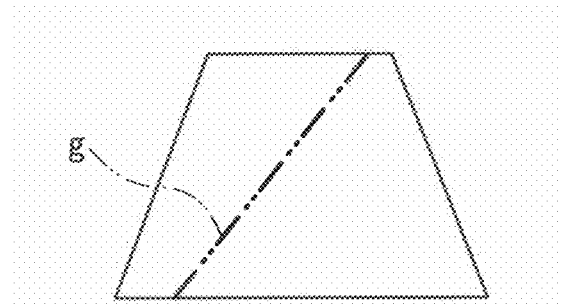
FIGS. 12A, 12B, and 12C are diagrams showing display examples of a puncture guideline in a three-dimensional scanning in the related art.
Figure 12B:
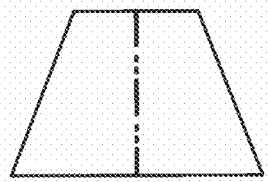
Figure 12C:
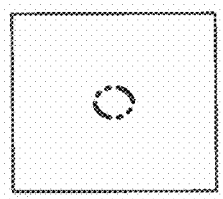

FIGS. 12A, 12B and 12C are diagrams showing display examples of a puncture guideline g in the three-dimensional scanning in the related art.

FIG. 12A shows an image of a first cross-section (A plane) on a preset puncture guideline g, FIG. 12B shows an image of a second cross-section (cut plane) perpendicular to the first cross-section and on the preset puncture guideline g, and FIG. 12C shows an image of a third cross-section (cut plane) perpendicular to the second cross-section. Each image is displayed as a moving image. With the related art, the first coordinate is set in the position of a puncture target where the needle-tip portion of the puncture needle 11a is finally inserted. However, if the needle-tip portion of the puncture needle 11a inserted into the body goes beyond the puncture guideline g, the image of the puncture needle 11a disappears from each image, and the operator cannot visually recognize the position of the puncture needle 11a.

Figure 13A:
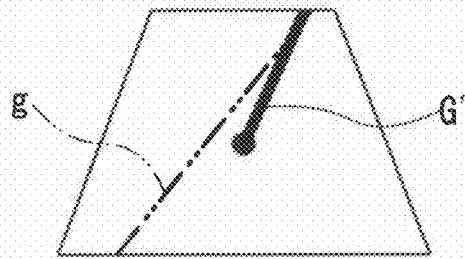
FIGS. 13A, 13B, and 13C are diagrams showing display examples of a puncture line in the three-dimensional scanning in the present embodiment.
Figure 13B:
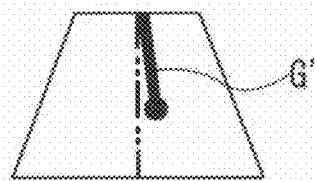
Figure 13C:
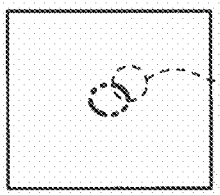

FIGS. 13A, 13B and 13C are diagrams showing display examples of a puncture line G in the three-dimensional scanning in the present embodiment.

FIGS. 13A, 13B and 13C show images having the same cross-sections as in FIGS. 12A, 12B and 12C. The puncture line G of the puncture needle 11a is calculated based on the first coordinate of the needle-tip portion actually detected by the composite image generating unit 33. Thus, when the puncture line G is in a three-dimensional coordinate system, a projection puncture line G' that is the puncture line G in the three-dimensional coordinate system projected on each cross-section can be displayed as shown in FIGS. 13A and 13B. As show in FIG. 13C, the image of the third cross-section can be displayed in a circle around an intersection between the puncture line G and the third cross-section to display an expected arrival position of the needle-tip portion of the puncture needle 11a. Thus, the operator can ascertain the precise position of the puncture needle 11a, and can perform quick and precise puncture. It may be conceivable that a cross-section position is automatically changed so that the puncture line G is displayed on each cross-section when the puncture needle 11a goes beyond the preset puncture guideline g.

The image memory 24 is controlled by the image generation control unit 31 to store the first image of a plurality of frames, the second image of a plurality of frames, and the third image of a plurality of frames. The composite image generating unit 33 generates a brightness maximum value image holding a maximum value of brightness that changes with time at each pixel based on the differential image, and generates a composite image based on the brightness maximum value image and a live third image. The composite image based on the brightness maximum value image and the live third image is sequentially generated and displayed, and thus the locus of the needle-tip portion of the puncture needle 11a is displayed as a moving image when the puncture needle 11a is inserted into the body, thereby increasing visibility of the puncture needle 11a in monitoring the puncture needle 11a. When an image holding a maximum value of brightness is generated using a third image in the related art, the maximum value of brightness is also held for a pixel of a substantial portion, and thus generation of the image holding the maximum value of brightness cannot be used.

The image generation control unit 31 in the ultrasonic diagnostic apparatus 10 is not limited to the case of generating the first image from the received signal based on the ultrasonic transmitting and receiving by scanning under the first transmitting/receiving condition at the low frequency, and generating the second image from the received signal based on the ultrasonic transmitting and receiving by scanning under the second transmitting/receiving condition at the high frequency. For example, it may be conceivable that the image generation control unit 31 controls the signal processing circuit 22 and the image generating circuit 23 to generate the first image from a fundamental component of the received signal based on the ultrasonic transmitting and receiving by scanning under the first transmitting/receiving condition, and generate the second image from a harmonic component of the received signal.

Figure 14:
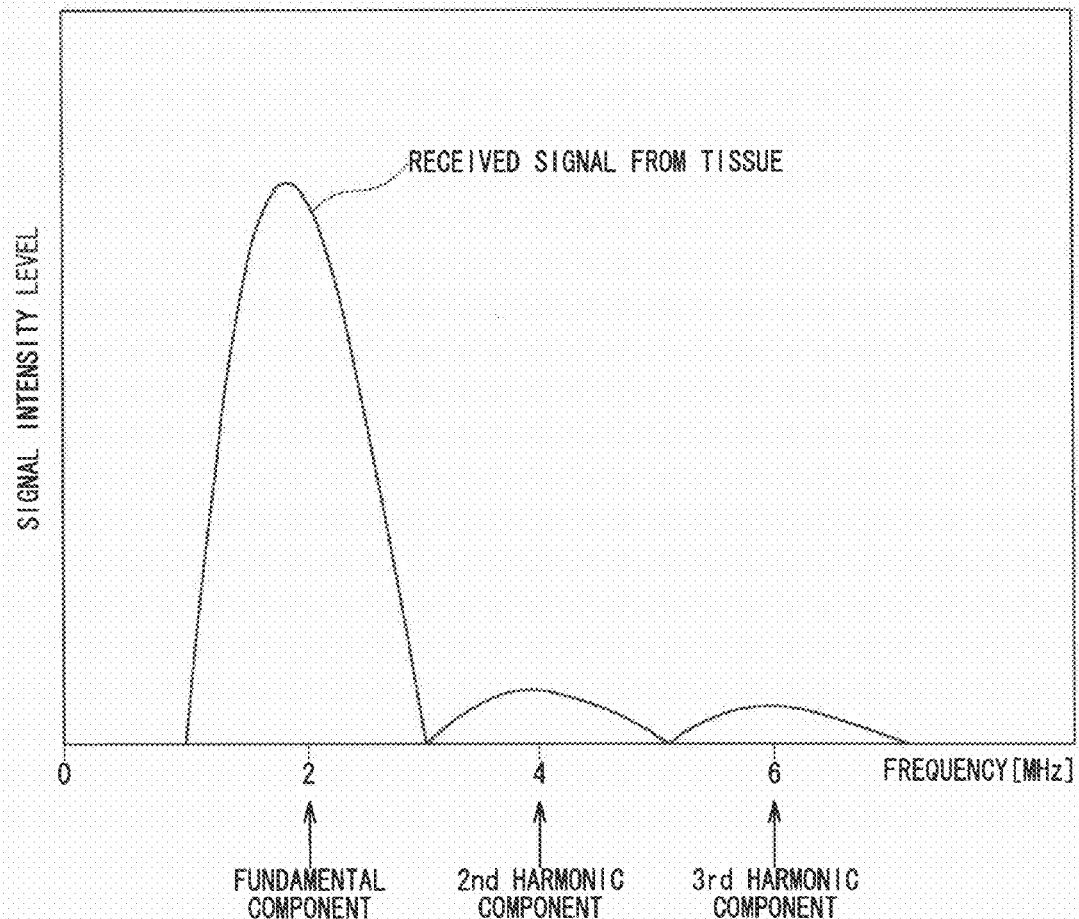
FIG. 14 is a diagram to explain a fundamental component and a harmonic component of a received signal.

FIG. 14 is a diagram to explain the fundamental component and the harmonic component of the received signal.

FIG. 14 shows a frequency spectrum of the received signal with the abscissa representing the frequency [MHz] and the ordinate representing the signal intensity level [dB]. As shown in FIG. 14, the received signal includes the fundamental component and the harmonic component (second harmonic component, third harmonic component). The fundamental component of the received signal includes much information on the needle-tip portion of the puncture needle 11a, while the harmonic component of the received signal includes little information on the needle-tip portion of the puncture needle 11a.

Further, pulse invention may be applied to the image generation control unit 31 shown in FIG. 2. The image generation control unit 31 may control the signal processing circuit 22 and the image generating circuit 23 to generate a first image from the fundamental component of the received signal by scanning under the first transmitting/receiving condition, and generate a second image from a secondary harmonic component of an additional signal of the received signal by scanning under the first transmitting/receiving condition, and the received signal by scanning under the second transmitting/receiving condition, including a transmission pulse waveform having a phase opposite to a transmission pulse waveform included in the first transmitting/receiving condition.

Figure 15:
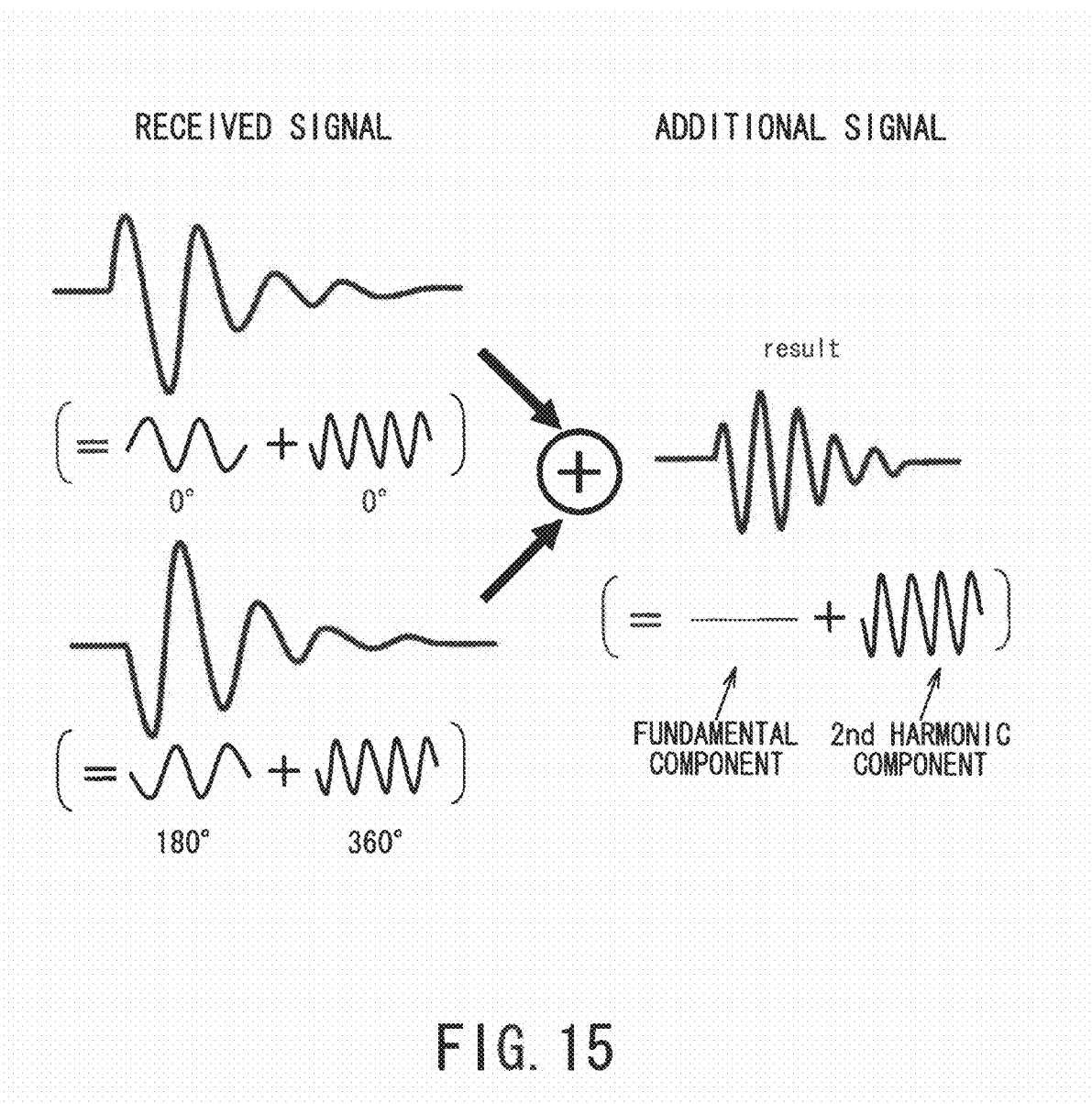
FIG. 15 is a diagram to explain an additional signal based on the received signals corresponding to two lines.

FIG. 15 is a diagram to explain the additional signal based on the received signals corresponding to two lines.

As shown in FIG. 15, the additional signal is obtained by adding the received signal by scanning under the first transmitting/receiving condition on the upper left side and the received signal by scanning under the second transmitting/receiving condition on the lower left side.

According to the ultrasonic diagnostic apparatus 10 of the present embodiment, the image of the object P including the needle-tip portion is displayed with only the needle-tip portion of the puncture needle 11a enhanced in monitoring the puncture needle 11a, thereby allowing the operator to easily visually recognize the position of the needle-tip portion.

What is claimed is:

1. An ultrasonic diagnostic apparatus comprising:
   an ultrasonic probe configured to transmit an ultrasonic pulse to a two-dimensional scanning region or a three-dimensional scanning region, and to receive an echo corresponding to the ultrasonic pulse as a received signal;
   a processor configured to:
      control the ultrasonic probe so as to perform scanning by sequential scanning lines in the scanning region, and sequentially perform a transmitting and receiving under a first imaging condition and a transmitting and receiving under a second imaging condition which is different from the first imaging condition in a same cross-section;
      generate a first image obtained by processing the received signal under the first imaging condition and a second image obtained by processing the received signal under the second imaging condition, the first and second images being images in which signal intensity is expressed by brightness;
      perform a differential processing between the first image and the second image to generate a differential image; and
      perform a composite processing between the differential image output from the differential processing and a medical image to generate a composite image.

2. The ultrasonic diagnostic apparatus according to claim 1, wherein
   the processor makes, when the scanning region includes a needle-tip portion of a puncture needle in an object, the ultrasonic probe perform the transmitting and receiving under the first and second imaging conditions, by changing in the first and second imaging conditions at least one of a transmitting condition in transmitting the ultrasonic pulse or a receiving condition in receiving the echo corresponding to the ultrasonic pulse, the first imaging condition being set so that an echo from the needle-tip portion is relatively stronger than a substantial portion other than the needle-tip portion compared to in the second imaging condition, and the second imaging condition being set so that the echo from the needle-tip portion of the puncture needle is relatively weaker than the substantial portion compared to in the first imaging condition.

3. The ultrasonic diagnostic apparatus according to claim 2, wherein the processor is further configured to perform a gain correction processing on the first image and the second image to generate a first corrected image and a second corrected image, wherein
   the processor performs the differential processing between the first corrected image and the second corrected image.

4. The ultrasonic diagnostic apparatus according to claim 2, wherein
   the processor sets a limited region including a guideline of the puncture needle in the first image or the differential image, and
   the processor performs the composite processing between the limited region, set in the first image or the differential image, and the entire region of the medical image.

5. The ultrasonic diagnostic apparatus according to claim 2, further comprising a filter configured to perform a filtering processing for removing a frequency band higher than a threshold from the first image or the differential image, wherein the processor performs the composite processing between the filtered first image or the filtered differential image, and the medical image.

6. The ultrasonic diagnostic apparatus according to claim 5, wherein
the filter performs the filtering processing on only a limited region, the limited region including a guideline of the puncture needle, and
the processor performs the composite processing between the limited region set in the filtered first image or the filtered differential image, and the entire region of the medical image.

7. The ultrasonic diagnostic apparatus according to claim 2, wherein
the processor generates a plurality of the first images corresponding to a plurality of frames, a plurality of the second images corresponding to a plurality of frames, and a plurality of the medical images corresponding to a plurality of frames, respectively,
the processor performs the differential processing between one of the first images and one of the second images to generate the differential image, and
the processor performs the composite processing between the differential image and one of the medical images to generate the composite image.

8. The ultrasonic diagnostic apparatus according to claim 7, wherein
the processor generates, for each frame, a brightness maximum value image holding a maximum value of brightness of the first images or the differential images, that changes with time at each pixel, and performs a composite processing between the brightness maximum value images and the medical images.

9. The ultrasonic diagnostic apparatus according to claim 7, wherein the processor generates first volume data in which the plurality of the first images of the three-dimensional scanning region under the first imaging condition are processed, generates second volume data in which the plurality of the second images of the three-dimensional scanning region under the second imaging condition are processed, and generates third volume data in which the plurality of the medical images of the three-dimensional scanning region under the third imaging condition are processed.

10. The ultrasonic diagnostic apparatus according to claim 9, wherein the processor is further configured to detect a position of the needle-tip portion from the first volume data, or differential volume data between the first volume data and the second volume data, calculate a puncture line of the puncture needle in the three-dimensional scanning region from the position of the needle-tip portion and positional information of a puncture adaptor including the puncture needle, and add the puncture line to the composite image.

11. The ultrasonic diagnostic apparatus according to claim 10, wherein
the processor generates three cross-sectional images perpendicular to each other as the composite image, and projects the position of the needle-tip portion on the three cross-sectional images.

12. The ultrasonic diagnostic apparatus according to claim 2, wherein
the processor sets transmitting conditions of the first imaging condition and the second imaging condition to be identical, and sets receiving conditions thereof to be different.

13. The ultrasonic diagnostic apparatus according to claim 12, wherein the processor sets the first imaging condition as a condition for visualizing a relatively low frequency band of the received signal compared to a frequency band of the received signal in the second imaging condition, and sets the second imaging condition as conditions for visualizing a relatively narrow and relatively high frequency band of the received signal compared to the frequency band of the received signal in the first imaging condition.

14. The ultrasonic diagnostic apparatus according to claim 12, wherein
the processor sets a relatively broad beam sound field and a relatively broad receiving opening of the ultrasonic probe as the first imaging condition, and sets a relatively narrow beam sound field and a relatively narrow receiving opening of the ultrasonic probe as the second imaging condition.

15. The ultrasonic diagnostic apparatus according to claim 1, wherein
the processor controls the ultrasonic probe so as to perform scanning by sequential scanning lines in the scanning region, and sequentially perform the transmitting and receiving under the first imaging condition, the transmitting and receiving under the second imaging condition, and a transmitting and receiving under a third imaging condition in the same cross-section, the third imaging condition being different from the first and second imaging conditions,
the processor generates the first image, the second image, and a third image obtained by processing the received signal under the third imaging condition, the first, second and third images being images in which signal intensity is expressed by brightness, and
the processor performs the composite processing between the differential image and the third image to generate the composite image.

16. The ultrasonic diagnostic apparatus according to claim 1, wherein the first and the second imaging conditions are different in a receiving condition of the echo corresponding to the ultrasonic pulse.

17. The ultrasonic diagnostic apparatus according to claim 1, wherein the first and the second imaging conditions are different.

18. An ultrasonic diagnostic method making an ultrasonic probe transmit an ultrasonic pulse to a two-dimensional scanning region or a three-dimensional scanning region, and making the ultrasonic probe receive an echo corresponding to the ultrasonic pulse as a received signal, comprising:
controlling the ultrasonic probe so as to perform, scanning by sequential scanning lines in the scanning region, and to sequentially perform a transmitting and receiving under a first imaging condition and a transmitting and receiving under a second imaging condition which is different from the first imaging condition in a same cross-section;
basic image generating which generates a first image obtained by processing the received signal under the first imaging condition and a second image obtained by processing the received signal under the second imaging condition, the first and second images being images in which signal intensity is expressed by brightness;
differential image generating which performs a differential processing between the first image and the second image to generate a differential image; and
composite image generating which performs a composite processing between the differential image and a medical image to generate a composite image.

19. The ultrasonic diagnostic method according to claim 18, wherein the controlling makes, when the scanning region includes a needle-tip portion of a puncture needle in an object, the ultrasonic probe perform the transmitting and receiving under the first and second imaging conditions, by changing in the first and second imaging conditions at least one of a transmitting condition in transmitting the ultrasonic pulse or a receiving condition in receiving the echo corresponding to the ultrasonic pulse, the first imaging condition being set so that an echo from the needle-tip portion is relatively stronger than a substantial portion other than the needle-tip portion compared to in the second imaging condition, and the second imaging condition being set so that the echo from the needle-tip portion of the puncture needle is relatively weaker than the substantial portion compared to in the first imaging condition.

20. The ultrasonic diagnostic method according to claim 18, wherein the controlling controls the ultrasonic probe so as to perform scanning by sequential scanning lines in the scanning region, and sequentially performs the transmitting and receiving under the first imaging condition, the transmitting and receiving under the second imaging condition, and a transmitting and receiving under a third imaging condition in the same cross-section, the third imaging condition being different from the first and second imaging conditions, the basic image generating generates the first image, the second image, and a third image obtained by processing the received signal under the third imaging condition, the first, second and third images being images in which signal intensity is expressed by brightness, and the composite image generating performs the composite processing between the differential image and the third image to generate the composite image.

\* \* \* \* \*